United States Patent [19]
Feierbach

[11] Patent Number: 5,861,018
[45] Date of Patent: Jan. 19, 1999

[54] ULTRASOUND TRANSDERMAL COMMUNICATION SYSTEM AND METHOD

[75] Inventor: Gary F. Feierbach, Belmont, Calif.

[73] Assignee: Telecom Medical Inc., San Francisco, Calif.

[21] Appl. No.: 655,129

[22] Filed: May 28, 1996

[51] Int. Cl.$^6$ .................................................. A61B 19/00
[52] U.S. Cl. ............................................ 607/60; 128/899
[58] Field of Search ................................... 128/899, 903; 607/32, 33, 60, 61, 34

[56] References Cited

U.S. PATENT DOCUMENTS

| | | | |
|---|---|---|---|
| 4,166,470 | 9/1979 | Neumann | 607/33 |
| 4,543,953 | 10/1985 | Slocum et al. . | |
| 4,571,589 | 2/1986 | Slocum et al. . | |
| 5,314,457 | 5/1994 | Jeutter et al. | 607/60 |
| 5,368,040 | 11/1994 | Carney . | |
| 5,383,915 | 1/1995 | Adams | 607/60 |
| 5,387,259 | 2/1995 | Davidson . | |
| 5,391,190 | 2/1995 | Pederson et al. . | |
| 5,626,630 | 5/1997 | Markowitz et al. | 607/60 |
| 5,630,836 | 5/1997 | Prem et al. | 607/60 |

*Primary Examiner*—William E. Kamm
*Assistant Examiner*—George R. Evanisko

[57] ABSTRACT

A system for communicating through the skin of a patient, the system including an internal communication device implanted inside the body of a patient and an external communication device. The external communication device includes an external transmitter which transmits a carrier signal into the body of the patient during communication from the internal communication device to the external communication device. The internal communication device includes an internal modulator which modulates the carrier signal with information by selectively reflecting the carrier signal or not reflecting the carrier signal. The external communication device demodulates the carrier signal by detecting when the carrier signal is reflected and when the carrier signal is not reflected through the skin of the patient. When the reflected carrier signal is detected, it is interpreted as data of a first state, and when the reelected carrier signal is not detected, it is interpreted as data of a second state. Accordingly, the internal communication device consumes relatively little power because the carrier signal used to carry the information is derived from the external communication device. Further, transfer of data is also very efficient because the period needed to modulate information of either the first state or the second state onto the carrier signal is the same. In one embodiment, the carrier signal operates in the ultrasound frequency range.

19 Claims, 5 Drawing Sheets

FIG. 5C

ULTRASOUND TRANSDERMAL COMMUNICATION SYSTEM AND METHOD

CROSS REFERENCE TO RELATED APPLICATIONS

Co-pending U.S. patent application Ser. No. 08/593,951, entitled "Transdermal Communication System and Method," U.S. patent application Ser. No. 08/549,375 entitled "System and Method to Monitor a Physiological Attribute of a Patient," filed Oct. 27, 1995, now U.S. Pat. No. 5,743,267 and U.S. patent application Ser. No. 08/545,306 entitled "System and Method to Measure the Condition of a Patient's Heart", filed Oct. 19, 1995, now U.S. Pat. No. 5,758,652 are incorporated by reference herein for all purposes.

BACKGROUND OF THE INVENTION

1. Field of the Invention

The present invention relates to an ultrasound communication system having an internal communication device imbedded in a confined exclosure and separated from an external communication device by a medium capable of transmitting ultrasonic frequency signals, and more particularly, to a communication system wherein data stored in the internal communication device is transferred to the external communication device by modulating an ultrasound carrier signal, transmitted by the external communication device, with the data by either reflecting the carrier signal or not reflecting the carrier signal, and recovering the data at the external communication device by detecting when the carrier signal is either reflected or not reflected through the medium.

2. Background Art

With recent advances in the field of microelectronics, it is now common to subdermally implant semiconductor chips and related circuitry into the body of a patient. The chips and circuitry are used to control a variety of bodily functions, and/or monitor anyone of a number of physiological attributes of a patient. For example, U.S. Pat. No. 5,391,190 entitled "Variation in Cardiac Chamber Volume or Pressure as a Controlling Parameter" issued to Pederson on Feb. 21, 1995, discloses the use of a cardiac pacemaker system that uses a subdermally implanted microprocessor to control the heart beat rate of the patient based on a heart and respiratory measurement. In yet another example, Carney in U.S. Pat. No. 5,368,040 entitled "Apparatus and Method for Determining A Plurality of Hemodynamic Variables From A Single Chronically Implanted Absolute Pressure Sensor", issued Nov. 29, 1994, discloses a telemetry system wherein circuitry subdermally implanted into a patient is used to transmit blood pressure measurements to a receiver external to the body.

One problem confronting bio-medical engineers developing transdermal communication devices is providing electrical power to the chronically implanted circuitry inside the body. The majority of implanted devices are powered using a battery. The power of the battery eventually drains, and needs to be replaced. The most common way to replace the battery is through surgery. Prior to the expiration of the battery, an operation is performed on the patient and either the battery is replaced, or a new device is implanted into the patient. Surgery, however, is usually a major ordeal for the patient, is costly, and is generally undesirable. Another way to provide power to an implanted device is through the use of a split transformer, where one coil of the transformer is located underneath the skin and the other coil is positioned outside the skin. The transformer is used to replenish power to an implanted power supply, such as a battery, when needed. See for example the above referenced Carney patent. The problem with transformers is that they require a coil to be implanted under the skin. The implanted coil also creates a widely dispersed alternating magnetic field which may interfere with other devices, such as pacemakers.

Another problem confronting bio-medical engineers is providing two-way communication through the skin of the patient. It is known to surgically implant wires through the skin of the patient. While this approach facilities two-way communication, it is generally undesirable. Chronically implanted wires piercing the skin tend to be uncomfortable for the patient, are unsanitary, and may cause infection. Radio telemetry is another known approach for communicating between an implanted device and an external device. With radio telemetry, data is transmitted either into or out of the body using radio waves. The problem with radio telemetry is that a transmitter/receiver is needed inside the body of the patient. These transmitter/receivers tend to be very sophisticated and expensive. Furthermore, the transmitter/receiver inside the body consumes a relatively large amount of power, particularly during broadcasting. In battery powered radio telemetry transdermal communication devices, the frequent broadcasting of data from the body to an external receiver tends to significantly reduce the life of the battery.

U.S. Pat. No. 5,387,259 entitled "Optical Transdermal Linking Method for Transmitting Power and Receiving an Internal Data Stream While Receiving a Second Data Stream,", issued to Davidson on Feb. 7, 1995, discloses an optical transdermal system. The system of Davidson provides an internal module implanted underneath the skin of a patient, and an external module. The internal module includes a photodetector, a preamplifier, a clock recovery circuitry for detecting an incoming optical signal, a laser diode and driver for transmitting an optical signal, and a photo-cell for providing power to the internal module. The external module includes one or more laser diodes for transmitting an optical signal to the internal module, and a photodetector for receiving an optical signal from the internal module. Davidson teaches two ways in which power can be provided to the internal module. One way is to provide the external module with an unmodulated laser diode which is dedicated for power transmission and a second laser diode dedicated for data transmission. Alternatively, a single laser diode can be used for both power transmission and data transmission. Regardless of the number of laser diodes used in the external module, the photo-cell of the internal module absorbs light transmitted through the skin of the patient by the laser diode of the external module. The light energy is then converted to electrical energy for powering the internal module.

A problem associated with the system of Davidson is that it requires the transmission of a relatively high power optical energy signal into the body to provide and replenish power to the internal module. The internal module also requires a photo-cell to convert the light energy into electrical energy. This process is generally inefficient, particularly through the skin and tissue of the patient. The internal module is also required to drive its own laser diode when transmitting data external to the body. Laser diodes consume a relatively large amount of power, which tends to drain the power of the photo-cell. Consequently, the Davidson device is less than ideal because the patient would be required to repeatedly replenish the photo-cell of the internal module.

U.S. Pat. No. 4,571,589 entitled "Biomedical Implant with High Speed, Low Power Two Way Telemetry", issued to Slocum on Feb. 18, 1986 discloses a transdermal communication system that relies on an external coil and an internal coil implanted under the skin of a patient. During data transmission from inside to outside of the body, the external coil generates a 64 KHz carrier signal. The impedance of the internal coil is then modulated using a switch. For example, in transmitting a binary zero, the carrier signal is modulated for two cycles. With a binary one, the carrier is modulated for six cycles. The modulated carrier signal is then re-radiated by the internal coil to the external coil. The re-radiated signal is then demodulated to recover the transmitted data by measuring the length of time in which the impedance of the internal coil is modulated by the switch. The problem with this arrangement is that modulation of the data, particularly a binary one, takes up to six cycles.

Accordingly, a transdermal communication system is needed wherein the energy required for communication between the internal and external communication devices is substantially provided by the external communication device and wherein the data transfer from the internal communication device to the external communication device is efficient.

SUMMARY OF THE INVENTION

The present invention relates to a transdermal communication system. The system includes an internal communication device implanted inside the body of a patient and an external communication device. The external communication device includes an external transmitter which transmits a carrier signal into the body of the patient during communication from the internal communication device to the external communication device. The internal communication device includes an internal modulator which modulates the carrier signal with information by selectively reflecting the carrier signal or not reflecting the carrier signal. The external communication device demodulates the carrier signal by detecting when the carrier signal is reflected and when the carrier signal is not reflected through the skin of the patient. When the reflected carrier signal is detected, it is interpreted as data of a first state, and when the reflected carrier signal is not detected, it is interpreted as data of a second state.

The present invention provides a number of advantages. The internal communication device consumes relatively little power because the carrier signal used to carry the information is derived from the external communication device. The transfer of data is also very efficient because the period needed to modulate information of either the first state or the second state onto the carrier signal is the same.

In one embodiment of the invention, the carrier signal is in the ultrasound frequency range. The use of ultrasound signals provides a number of advantages. As best understood by medical science, ultrasound signals pose no danger to humans. Ultrasound signals do not interfere with other medical device, such as pace makers, as does microwave signals. The use of ultrasound can also be very hospitable with humans. The recommended frequency range is well above the audible range of most humans, and therefore can not be heard.

DESCRIPTION OF THE DRAWINGS

The features and advantages of the present invention will be apparent from the following description in which:

FIGS. 5A through 5E illustrate a series of signals that are generated in the transdermal communication device of the present invention during external to internal communication.

DESCRIPTION OF THE PREFERRED EMBODIMENT

Figure 1:
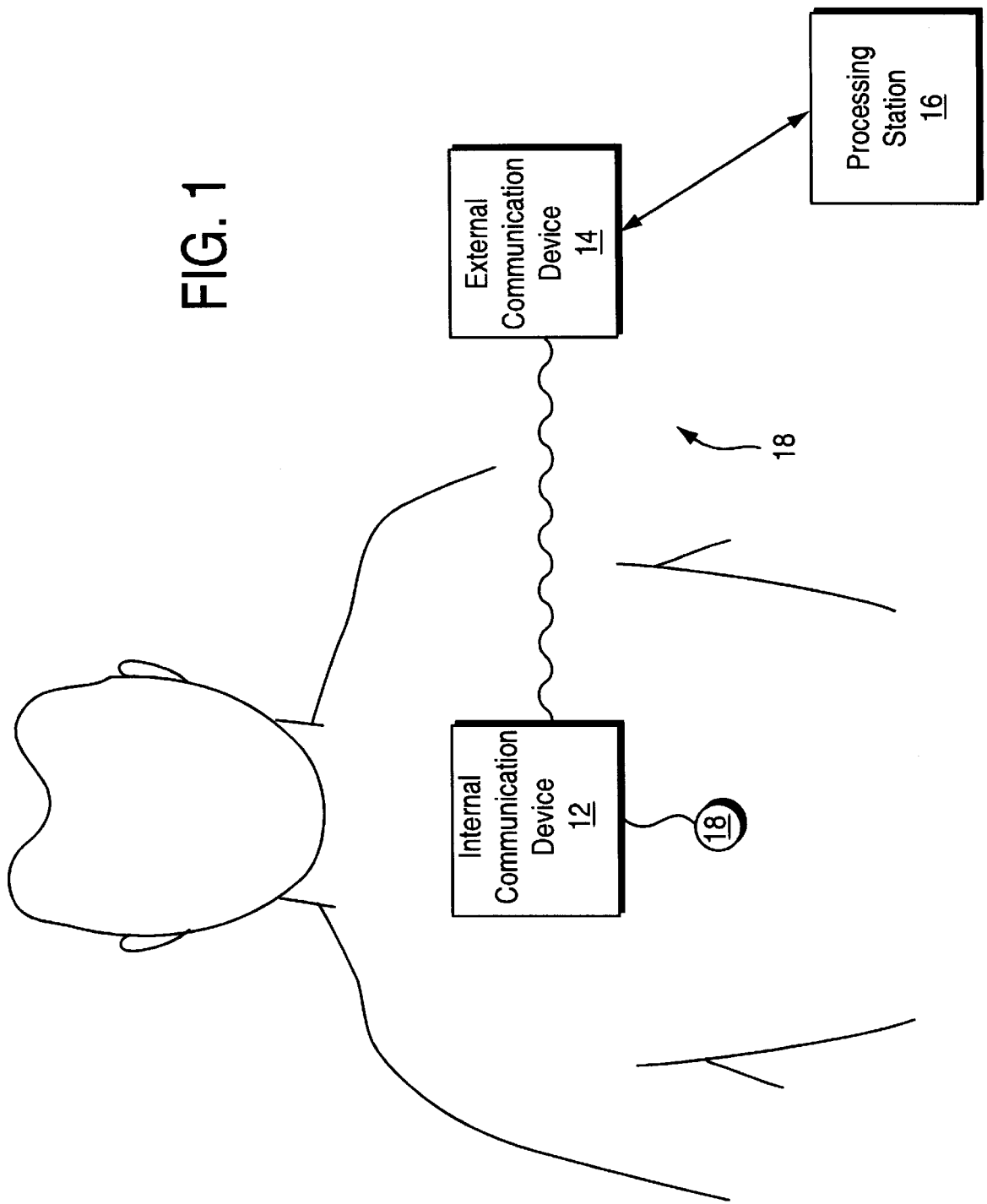
FIG. 1 is a block diagram of the transdermal communication device of the present invention.

Referring to FIG. 1, a block diagram of a transdermal communication system of the present invention is shown. The communication device 10 includes an internal communication device 12, an external communication device 14, and a processing station 16. The internal communication device 12 is coupled to a measuring device 18. The internal communication device 12 and the measuring device 18 are both implanted in the body of a patient. According to various embodiments of the invention, the measuring device 18 measures any physiological attribute of the patient, and generates an absolute signal indicative of the measured attribute. The internal communication device 12 receives the absolute signal and performs one or more data processing operations on the absolute signal. The internal communication device 12 then temporarily stores the processed data. Upon the direction of the patient, the internal communication device 12 transfers the stored data to the external communication device 14 through the skin of the patient. The external communication device 14 transfers the processed data to the processing station 16, where the data is further processed and analyzed. The processing station 16 presents the data related to the measured physiological attribute to a doctor or other medical personnel, who then may monitor the physiological attribute of the patient, and may subscribe a treatment for the patient if needed. The external communication device 14 can also be used to communicate information from the processing station 16 to the internal communication device 12. Such information may include a computer program used to control the internal communication device 12, updates to a computer program previously stored in the internal communication device 12, or control information directing the internal communication device 12 to sample the absolute signal at a specific time or times.

In one embodiment, the measuring device 18 is a blood pressure sensor implanted into the heart of the patient. The blood pressure sensor generates a signal indicative of the absolute blood pressure in the heart of the patient. The internal communication device 12 contains circuitry that samples the absolute blood pressure signal, and generates a filtered blood pressure signal in response thereto. The circuitry in the internal communication device 12 then analyzes the filtered blood pressure signal, and then generates a set of parameters indicative of the condition and strength of the heart of the patient. The set of parameters are then temporarily stored in the internal communication device 12. The set of parameters are then subsequently transferred to the external communication device 14, and the processing station 16 for further processing and analysis. For more information regarding this embodiment, see the above mentioned parent applications. In alternative embodiments, the circuitry of the internal communication device 12 may be used to process, filter and generate parameters for any physiological attribute of the patient. Such physiological attributes may include, but are not limited to, ecg, chemical, hormonal, digestive, neural, or any organ in the body including, but not limited to, the brain, heart, lungs, kidneys, liver, blood, bladder, etc.

Figure 2:
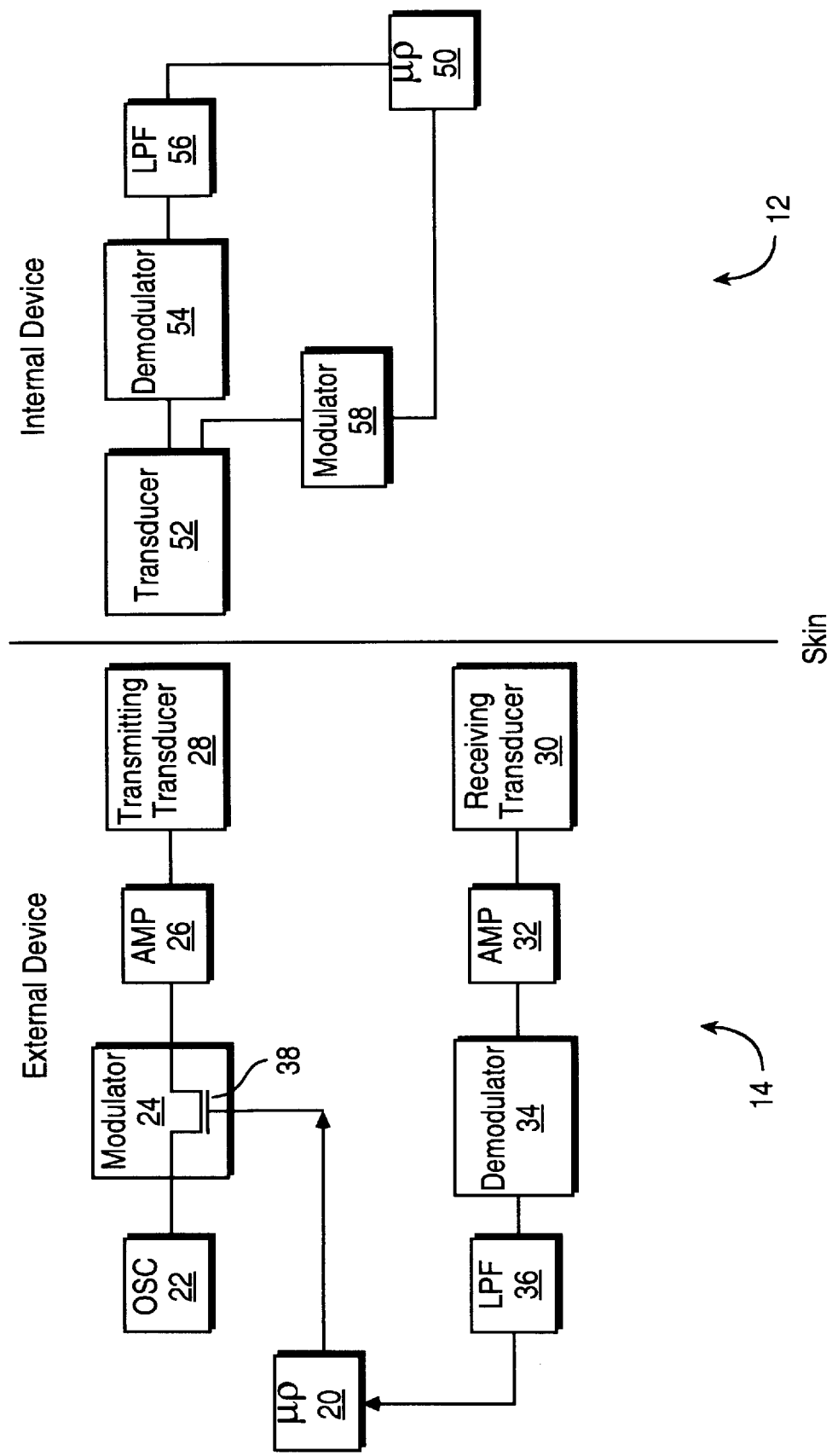
FIG. 2 is a logic diagram of an internal communication device and an external communication device of the present invention.

Referring to FIG. 2, a block diagram of the transdermal communication system 10 of the present invention is shown. The transdermal communication device 10 includes the internal communication device 12 and the external communication device 14.

The external communication device 14 includes a microprocessor 20, an oscillator 22, a modulator 24, an amplifier 26, a transmitting transducer 28, a receiving transducer 30, a second amplifier 32, a demodulator 34, and a low pass filter 36. The microprocessor 20 is a standard microprocessor, such as model number 68HC11FN from Motorola. The oscillator 22 is an oscillator that generates a constant ultrasound frequency signal ranging anywhere from 20 KHz to 10 MHz or higher, depending on the desired rate of data transfer. In one embodiment, the modulator 24 includes an FET 38. The FET 38 has its source and drain coupled between the oscillator 22 and the amplifier 26. The gate of the FET 38 is coupled to and controlled by the microprocessor 20. The amplifier 26 is a standard audio amplifier, such as a Darlington configuration. The transmitting transducer 28 is a mechanical transducer, such as an audio speaker, that is capable of receiving an electrical signal of a given frequency and amplitude, and converting it into a mechanical signal of a corresponding frequency and amplitude. The receiving transducer 30 is a ultrasound resonator that is capable of converting a mechanical signal of a given frequency and amplitude into an electrical signal having a corresponding frequency and amplitude.

Figure 3:
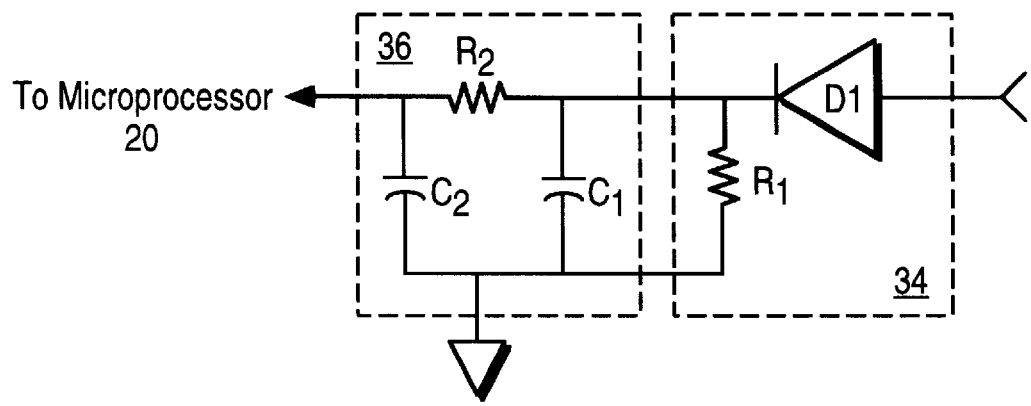
FIG. 3 is a circuit diagram of a demodulator and a low pass filter used in the present invention.

Referring to FIG. 3, a circuit diagram of the demodulator 34 and the low pass filter 36 is shown. The demodulator 34 includes a diode D1 and resistor R1. The low pass filter 36 includes resistor R2 and capacitors C1 and C2. The amplifier 32 is also a standard audio amplifier, such as a Darlington.

The internal communication device 12 includes a microprocessor 50, a receiving and transmitting transducer 52, a demodulator 54, a low pass filter 56, and a modulator 58. The microprocessor 50 is a low powered chip, such as the model number PIC1671 by the Microchip Corporation, Chandler, Ariz. The receiving and transmitting transducer 52 is an ultrasound resonator that is capable of converting a mechanical signal of a given frequency and amplitude into an electrical signal having a corresponding frequency and amplitude. The demodulator 54 and low pass filter 56 demodulate and filter the signal generated by the receiving and transmitting transducer 52, and provide the resulting signal to the microprocessor 50. The demodulator 54 and the low pass filter 56 can be implemented using the same circuitry illustrated in FIG. 3. The modulator 58, which is controlled by the microprocessor 50, is used to control the receiving and transmitting transducer 52 when data is being transmitted from the internal device 12 to the external device 14.

Figure 4:
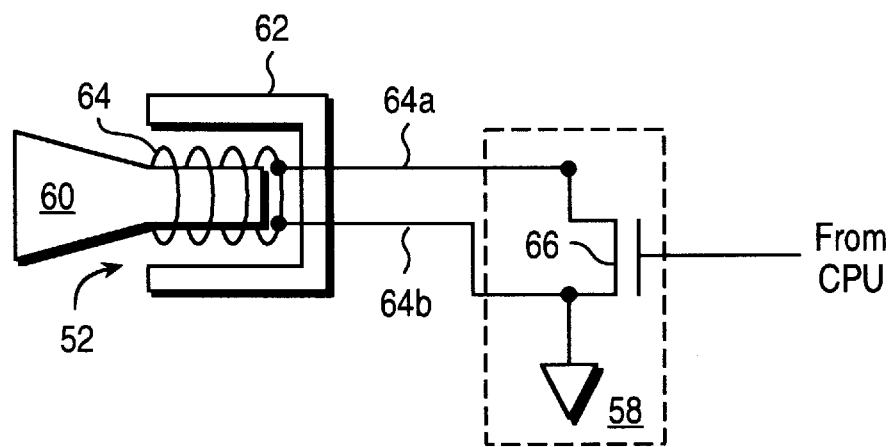
FIG. 4 illustrates a receiving and transmitting transducer and a modulator circuit according to the present invention.

Referring to FIG. 4, a detailed diagram of the receiving and transmitting transducer 52 and the modulator 58 is shown. The receiving and transmitting transducer 52 is essentially an audio speaker, and includes a cone 60, a magnet 62, and a voice coil 64 having two leads 64a and 64b. The demodulator 58, in one embodiment, is an FET 66. The gate of the FET 66 is coupled to and is controlled by the microprocessor 50. The lead 64a is coupled to the drain and the lead 64b is coupled to the source of the FET 66. The source of the FET 66 is coupled to ground.

The transmitting transducer 28, the receiving and transmitting transducer 52, and the receiving transducer 30 form a three-way mechanically coupled tuned circuit during communication between the external device 14 and the internal device 12. Each transducer has a Q value, and the tuned system as a whole has a coupled tuned value $Q_c$. In one embodiment, the coupled $Q_c$ value of the system is in the range of five to ten.

OPERATION

The communication device 10 is capable of bi-directional communication through the skin of the patient. Operation of both forms of communication is described below.

External to Internal Communication

Figure 5A:
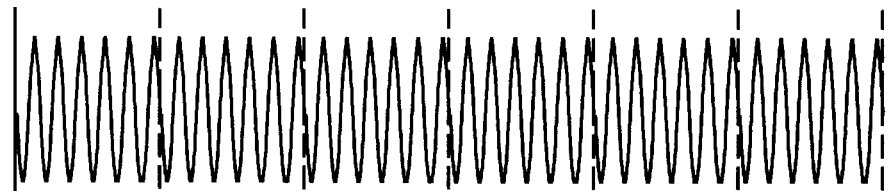
Figure 5B:
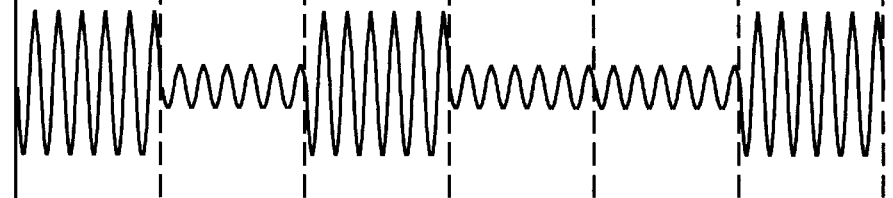

External to internal communication of the communication device 10 is best explained with reference to FIGS. 5A through 5E. With external to internal communication, the oscillator 22 generates a carrier signal at a given frequency in the above defined range, as illustrated in FIG. 5A. The modulator 24, under the control of the microprocessor 20, is used to modulate the information onto the carrier signal. This is accomplished by either activating or de-activating FET 38 of the modulator 24. For example, if a logical one is to be modulated onto the carrier signal, the FET 38 is activated, and the carrier signal is allowed to pass through the channel of the transistor to the input of the amplifier 26. On the other hand, if a logical zero is to be modulated onto the carrier signal, the FET is not activated. As a result, the carrier signal is not connected to the input of the amplifier 26. By way of example, FIG. 5B shows a modulated carrier signal with the digital information of (1, 0, 1, 0, 0, 1) modulated thereon during six consecutive time periods $t_0$ through $t_6$ respectively. This signal was generated by maintaining the FET 38 on during the time periods ($t_0$–$t_1$, $t_2$–$t_3$, $t_5$–$t_6$) and off during the time periods ($t_1$–$t_2$, $t_3$–$t_4$, $t_4$–$t_5$) respectively. The modulated carrier signal is then amplified by the amplifier 26 and provided to the input of the transmitting transducer 28. The transmitting transducer 28 receives the amplified and modulated carrier signal, and in response generates a mechanical signal having a corresponding frequency and amplitude. The resulting mechanical wave form is illustrated in FIG. 5C, and includes a relatively high amplitude in periods where a logical one was modulated onto the carrier signal, and a relatively low amplitude in periods where a logical zero was modulated onto the carrier signal respectively.

Figure 5D:
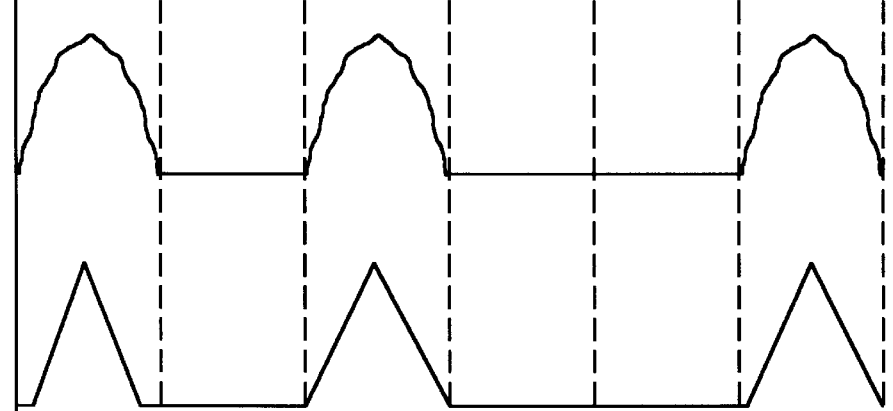
Figure 5E:
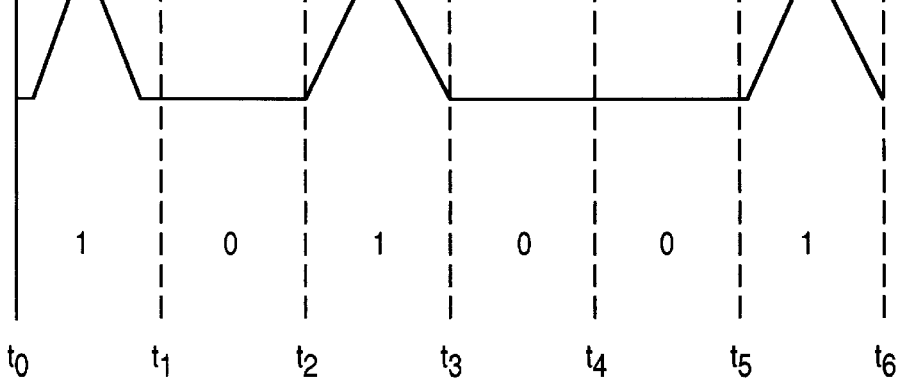

In the internal communication device 12, the receiving and transmitting transducer 52 receives the mechanical signal as illustrated in FIG. 5C through the skin of the patient. In the periods where a logical one is being transmitted, the cone 58 and the voice coil 64 move at a frequency and magnitude corresponding to the relatively high frequency and magnitude of the mechanical signal, inducing a voltage signal of corresponding frequency and amplitude in the coil 64. In the periods where a logical zero is being transmitted, the cone 58 and the voice coil 64 substantially do not move, thereby inducing a negligible voltage signal in the voice coil 64. The resulting electrical signal, with the digital information (1, 0, 1, 0, 0, 1) modulated thereon, is illustrated in FIG. 5D. The electrical signal from the receiving and transmitting transducer 52 is then provided to the demodulator 54 and the low pass filter 56. With periods ($t_1$–$t_2$, $t_3$–$t_4$, $t_4$–$t_5$) containing a logical zero, the voltage of the signal falls below the turn on voltage of the diode D1. As a result, the diode D1 remains off. With periods ($t_0$–$t_1$, $t_2$–$t_3$, $t_5$–$t_6$) containing a logical one, the diode D1 turns on, and the signal is applied to the low pass filter 56. The high frequency components of the signal are then removed by the low pass filter 56. The resulting signal, carrying the original digital information of (1, 0, 1, 0, 0, 1) as shown in FIG. 5E, is then provided to the microprocessor 50.

Internal to External Communication

With internal to external communication, an unmodulated carrier signal from the oscillator 22 of the external device 14 is transmitted through the skin of the patient. This is accomplished by activating the oscillator 22, and holding the FET 38 in the on state. The transmitting transducer 28 thus generates a continuous high amplitude mechanical signal having a frequency approximately the same as the oscillator 22. The transmitting and receiving transducer 52, which receives the mechanical signal through the skin of the patient, selectively reflects the mechanical signal to the receiving transducer 30 of the external device 14 during internal to external communication.

As best illustrated in FIG. 4, when the microprocessor 50 transmits a logical zero, it activates the FET 66 of the modulator 58. As a result, the leads 64a and 64b of the voice coil 64 are grounded. The Q value of the transmitting and receiving transducer 52 is consequently degraded, and the magnitude of the reflected mechanical signal received at the receiving transducer 30 is negligible. In transmitting a logical one, the microprocessor 50 maintains the FET 66 of the modulator 58 in an off state. The Q value of the transmitting and receiving transducer 52 returns to its normal value, and the receiving transducer 30 receives a relatively large amount of reflected mechanical energy. By selectively activating the modulator 58, the microprocessor 50 can transmit a stream of digital information to the external device 12 in the form of logical ones and zeros.

The receiving transducer 30 is also a audio speaker configured as a resonator. In the same manner as described above with respect to the receiving and transmitting transducer 52, the receiving transducer 30 converts the mechanical signal into a corresponding electrical signal. The amplifier 32, demodulator 34, and low pass filter then process the electrical signal, and provides the resulting data stream to the microprocessor 20.

Figure 6:
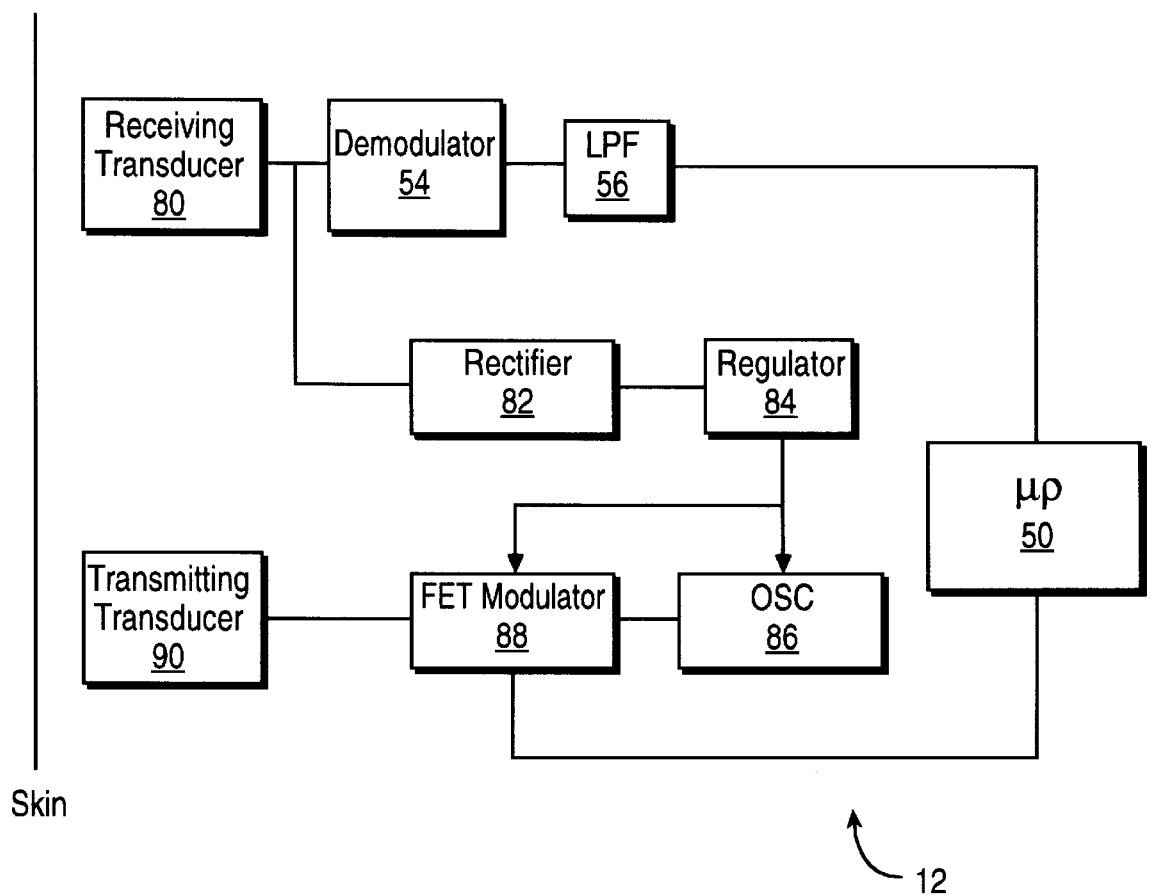
FIG. 6 illustrates a second embodiment of the internal communication device according to the present invention.

Referring to FIG. 6, a block diagram of the internal device 14 according to a second embodiment of the invention is shown. In this embodiment, the internal device 12 includes demodulator 54, low pass filter 56, microprocessor 50, receiving transducer 80, bridge rectifier 82, voltage regulator 84, oscillator 86, FET modulator 88, and transmitting transducer 90. The receiving transducer 80 operates the same as the receiving and transmitting transducer 52, except it is not used as a resonator during internal to external communication. Elements with the same reference numbers as provided in FIG. 2 perform the same or a similar function herein, and therefore are not described in detail herein. The operation of the external communication device 14 during external to internal and vice-versa communication and the operation of this embodiment during external to internal communication is essentially the same as that described above, and is again not described in detail herein.

During internal to external communication with this second embodiment, the receiving transducer 80 generates a continuous electrical signal having a frequency and amplitude corresponding to the mechanical signal generated by the transmitting transducer 28 of the external device 12. In response, the rectifier 82 generates a direct current signal from the electrical signal output from the receiving transducer 80. The regulator 84 generates a voltage from the direct current signal, which is then used to power the oscillator 86 and the FET modulator 88. The internal device 14 then transmits information to the external device 14 by modulating the carrier signal generated by the oscillator 86 with the modulator 88, and converting the modulated signal into a corresponding mechanical signal using the transmitting transducer 90. The receiving transducer 30 then receives and processes the mechanical signal in the same manner as described above, and the resulting data stream is provided to the microprocessor 20.

Although not described herein, it should be noted that the ultrasonic transdermal communication system 10 of the present invention can be used in the medical systems described in the above reference parent applications. For example, the communication system 10 can be used in conjunction with the housing, the alignment protocols, and the timing and data transfer protocols for communication to and from the communication system 10 and the processing station 16 via the housing.

The present invention provides a number of advantages. The internal communication device consumes relatively little power because the carrier signal used to carry the information is derived from the external communication device. The transfer of data is also very efficient because the period needed to modulate information of either the first state or the second state onto the carrier signal is the same. The use of ultrasound signals provides a number of advantages. As best understood by medical science, ultrasound signals pose no danger to humans. Ultrasound signals do not interfere with other medical device, such as pace makers, as does microwave signals. The use of ultrasound is also very hospitable with humans. This frequency range is generally well above the audible range of humans, and therefore can not be heard.

It should be noted that the digital information can be transmitted in accordance with any well known encoding scheme, such as NRZ, NRZI, or PWM. In an alternative embodiment of the invention, the carrier signal can be modulated with analog information.

Although the present invention was described in the context of a transdermal communication device, it should be noted that the present invention could be used with any medium capable of transmitting ultrasonic signals, such as metals, plastics, wood, glass, etc. The present invention is best suited for applications where communication is desired between a confined enclosure of some kind, and the outside world. Once the internal communication device is embedded in the enclosure, the present invention can be used for easy and efficient communication between the internal and external devices. It is intended that the specification be only exemplary, and that the true scope and spirit of the invention be indicated by the following claims.

I claim:

1. A communication system, comprising:
   a first communication device configured to be implanted inside an enclosure, the enclosure having a medium capable of transmitting communication signals;
   a second communication device configured to be located outside the enclosure;
   a second transmitter, coupled to the second communication device, and configured to generate a first carrier signal into the enclosure during communication from the first communication device to the second communication device;

a first receiver, coupled to the first communication device, and configured to receive the first carrier signal;

a first power generator, coupled to the first receiver, and configured to generate a power supply derived from the first carrier signal;

a first transmitter, coupled to the power supply, and configured to generate a second carrier signal from the power supply;

a first modulator, coupled to the first transmitter, and configured to modulate the second carrier signal with information to be transmitted from the first communication device to the second communication device;

a second receiver, coupled to the second communication device, and configured to receive the modulated second carrier signal; and a second demodulator, coupled to the second communication device, and configured to demodulate the modulated second carrier signal, the first receiver and the second transmitter configured to form a mechanically tuned circuit having a value of Q during transmission of information signals of a first logical state and a second Q value during transmission of second information signals of a second logical state during communication from the second communication device to the first communication device, the second receiver and the first transmitter further configured to form the mechanically tuned circuit having the first value of Q during transmission of information signals of the first logical state and the second Q value during transmission of second information signals of the second logical state during communication from the first communication device to the second communication device, whereby the information signals are communicated from the first communication device to the second communication device, or vice versa, by way of mechanical vibrations through the enclosure.

2. The system of claim 1, wherein the first communication device is further configured to be imbedded into the body of a patient and the first carrier signal and the second carrier signal are in the ultrasonic frequency range.

3. The system of claim 1, wherein the first communication device is configured to be imbedded into the body of a patient and the first carrier signal and the second carrier signal are in the ultrasonic frequency range.

4. The system of claim 1, wherein the first modulator modulates the second carrier signal with information of a first state during a first time interval during which the second carrier signal is transmitted and modulates the second carrier signal with the information of a second state during a second time interval during which the carrier signal is not transmitted.

5. The system of claim 4, wherein the first time interval and the second time interval are substantially the same in duration.

6. The system of claim 5, wherein the first modulator includes a transducer.

7. The system of claim 6, wherein the transducer is selectively dampened by a dampening circuit to selectively transmit or not transmit the second carrier signal.

8. The system of claim 7, further comprising a microprocessor to control the selective dampening of the transducer.

9. The system of claim 8, wherein the first modulator comprises a switch, coupled between the transducer and the microprocessor, the switch being selectively activated by the microprocessor to selectively dampen or not dampen the transducer.

10. The system of claim 6, wherein the transducer is an audio transducer.

11. The system of claim 1, wherein the second demodulator is a transducer configured to generate a first signal when the modulated second carrier signal is received at the second communication device and a second signal when the second carrier signal is not received at the second communication device.

12. The system of claim 11, further comprising a microprocessor, coupled to the second demodulator, and configured to interpret the first signal and the second signal.

13. The system of claim 1, wherein the second transmitter comprises an oscillator configured to generate the first carrier signal and a transducer coupled to the oscillator to transmit the carrier signal.

14. The system of claim 13, further comprising a second modulator, coupled between the oscillator and the transducer, and configured to modulate the first carrier signal during communication from the second communication device to the first communication device.

15. The system of claim 1, wherein the first Q value is in the range of five to ten and the second Q value is outside the range of five to ten.

16. A method of providing a communication system, comprising the steps of:

providing a first communication device configured to be implanted in an enclosure with a medium capable of transmitting communication signals;

providing a second communication device configured to be located outside the enclosure;

providing a second transmitter, coupled to the second communication device, and configured to transmit a first carrier signal into the enclosure during communication from the first communication device to the second communication device;

providing a first receiver, coupled to the first communication device, and configured to receive the first carrier signal;

providing a first power generator, coupled to the first receiver, and configured to generate a power supply derived from the first carrier signal;

providing a first transmitter, coupled to the power supply, and configured to generate a second carrier signal from the power supply;

providing a first modulator, coupled to the first transmitter, and configured to modulate the second carrier signal with information to be transmitted from the first communication device to the second communication device;

providing a second receiver, coupled to the second communication device, and configured to receive the modulated second carrier signal; and providing a second demodulator, coupled to the second communication device, and configured to demodulate the second carrier signal, the first receiver and the second transmitter configured to form a mechanically tuned circuit having a value of Q during transmission of information signals of a first logical state and a second Q value during transmission of second information signals of a second logical state during communication from the second communication device to the first communication device, the second receiver and the first transmitter further configured to form the mechanically tuned circuit having the first value of Q during transmission of information signals of the first logical state and the second Q value during transmission of second information signals of the second logical state during communication from the first communication device to the second communication device, whereby the information signals are communicated from the first communication device to the second communication device, or vice versa, by way of mechanical vibrations through the enclosure.

17. The method of claim 16, wherein the first Q value is in the range of five to ten and the second Q value is outside the range of five to ten.

18. A communication system, comprising:

a first communication device configured to be implanted inside an enclosure, the enclosure having a medium capable of transmitting communication signals;

a second communication device configured to be located outside the enclosure;

a second transmitter, coupled to the second communication device, and configured to generate a first carrier signal into the enclosure during communication from the first communication device to the second communication device;

a first receiver, coupled to a processing unit in the first communication device, and configured to receive the first carrier signal;

a first transmitter configured to generate a second carrier signal;

a first modulator, coupled to the first transmitter, and configured to modulate the second carrier signal with information to be transmitted from the first communication device to the second communication device;

a power generator coupled to the first modulator and the processing unit;

a second receiver, coupled to the second communication device, and configured to receive the modulated second carrier signal; and a second demodulator, coupled to the second communication device, and configured to demodulate the modulated second carrier signal, the first receiver and the second transmitter configured to form a mechanically tuned circuit having a value of Q during transmission of information signals of a first logical state and a second Q value during transmission of second information signals of second logical state during communication from the second communication device to the fist communication device.

the second receiver and the first transmitter further configured to form the mechanically tuned circuit having the first value of Q during transmission of information signals of the first logical state and the second Q value during transmission of second information signals of the second logical state during communication from the first communication device to the second communication device, whereby the information signals are communicated from the first communication device to the second communication device. or vice versa, by way of mechanical vibrations through the enclosure.

19. The system of claim 18, wherein the first Q value is in the range of five to ten and the second Q value is outside the range of five to ten.

\* \* \* \* \*